United States Patent [19]
Brown et al.

[11] Patent Number: 5,859,429
[45] Date of Patent: Jan. 12, 1999

[54] OPTICAL SYSTEM WITH TEST/CALIBRATION

[75] Inventors: Stephen Wayne Brown, Grapevine; Gregory Edward Gardner, Euless; Kristine Marie Garner, Rockwall; Carl Michael Oleksak, Burleson; James Alan Vaught, Bedford, all of Tex.

[73] Assignee: Abbott Laboratories, Abbott Park, Ill.

[21] Appl. No.: 915,029

[22] Filed: Aug. 20, 1997

[51] Int. Cl.⁶ ........................................ G01J 1/10
[52] U.S. Cl. .................. 250/252.1; 250/227.31; 250/559.1
[58] Field of Search .................. 250/559.1, 458.1, 250/459.1, 252.1 A, 227.31

[56] References Cited

U.S. PATENT DOCUMENTS

| | | | |
|---|---|---|---|
| 3,746,514 | 7/1973 | Colvin et al. | 250/218 |
| 3,754,866 | 8/1973 | Ritchie et al. | 23/253 R |
| 4,047,034 | 9/1977 | Auphan | 250/354 |
| 4,160,165 | 7/1979 | McCombs et al. | 250/354 |
| 4,256,960 | 3/1981 | Snider | 250/252 |
| 4,437,762 | 3/1984 | Glenn et al. | 356/326 |
| 4,517,460 | 5/1985 | Meulenbrugge et al. | 250/252.1 |
| 4,537,510 | 8/1985 | Takahasi | 356/435 |
| 4,602,154 | 7/1986 | Taniguchi | 250/227 |
| 4,802,768 | 2/1989 | Gifford et al. | 356/417 |
| 4,827,126 | 5/1989 | Tanaka | 250/235 |
| 4,954,882 | 9/1990 | Kamemoto | 358/22 |
| 5,004,904 | 4/1991 | Yamakawa et al. | 250/207 |
| 5,051,585 | 9/1991 | Koshishiba et al. | 250/306 |
| 5,079,424 | 1/1992 | Kobayashi | 250/369 |
| 5,315,375 | 5/1994 | Allen | 336/417 |
| 5,316,726 | 5/1994 | Babson et al. | 422/65 |
| 5,453,610 | 9/1995 | Gibbons | 250/207 |
| 5,500,371 | 3/1996 | Gleaves | 436/37 |
| 5,559,324 | 9/1996 | Rapkin et al. | 250/251.1 |
| 5,561,290 | 10/1996 | Strobel et al. | 250/252.1 |

FOREIGN PATENT DOCUMENTS

0346878  9/1994  European Pat. Off. .

*Primary Examiner*—Edward P. Westin
*Assistant Examiner*—Thanh Luu
*Attorney, Agent, or Firm*—Mark C. Bach

[57] ABSTRACT

Optical systems are provided. In one embodiment, the optical system includes a detector for detecting a light signal. A light signal gatherer and guider is optically connected with the detector for gathering the light signal and guiding the light signal to the detector. The light signal gatherer and guider has a check signal entrance location disposed along an outer surface of the light signal gatherer and guider. A check signal source is optically connected with the light signal gatherer and guider so that a check signal generated by the check signal source randomly illuminates the check signal entrance location on the outer surface of the light signal gatherer and guider.

11 Claims, 8 Drawing Sheets

OPTICAL SYSTEM WITH TEST/CALIBRATION

BACKGROUND

The following relates to an optical system and its method of operation.

Today, a number of machines, such as medical analyzers and the like, operate or otherwise perform their functions by looking at or reading a signal. In some cases, this signal may be a light signal generated by a particular marker or label attached to an item of interest. In order to read this light signal, these machines may use an optical system which gathers the light signal and guides the gathered light signal to a reader, such as an element that produces an electrical signal in response to the gathered and guided light signal.

For such machines to operate as intended, it is desirable to check or to calibrate the optical system from time to time. Depending on the type of machine involved, this checking may be rather difficult. Also, the method or device used to check the optical system may not always accurately check the optical system. Accordingly, it is desirable to provide an improved optical system.

SUMMARY

Optical systems are provided. In one embodiment, the optical system includes a detector for detecting a light signal. A light signal gatherer and guider is optically connected with the detector for gathering the light signal and guiding the light signal to the detector. The light signal gatherer and guider has a check signal entrance location disposed along an outer surface of the light signal gatherer and guider. A check signal source is optically connected with the light signal gatherer and guider so that a check signal generated by the check signal source randomly illuminates the check signal entrance location on the outer surface of the light signal gatherer and guider.

DETAILED DESCRIPTION OF ILLUSTRATED EMBODIMENTS

Figure 1:
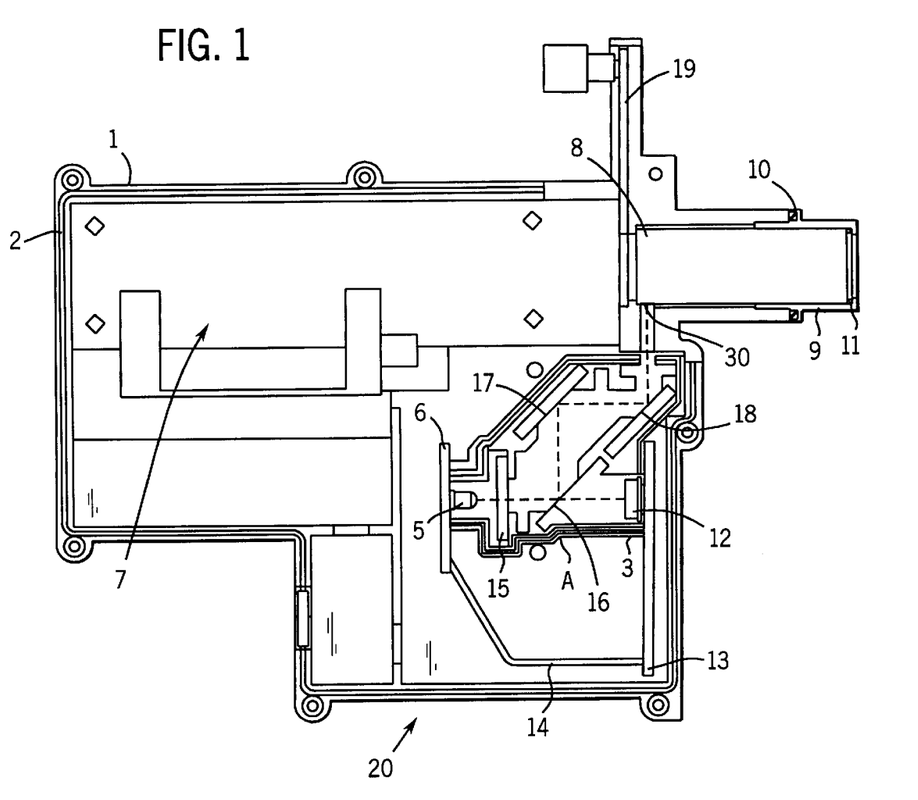
FIG. 1 is a cut-away view of an optical system described herein.

One embodiment of an optical system 20 is illustrated in FIG. 1. For the sake of clarity of understanding, the optical system 20 will be discussed with respect to a particular utilization or employment. For instance, the optical system 20 may be used with the constructions disclosed in co-pending U.S. patent applications, Ser. Nos. 08/715,924, 08/715,780 and 08/816,121 filed on Sep. 19, 1996. Those applications are assigned to the assignee of this case and the disclosures thereof are incorporated herein by this reference. It is to be noted, however, that the optical system 20, possibly with suitable modifications, may be used in other employments without departing from the scope of the appended claims.

For the purposes of this discussion, the optical system 20 is used to quantitatively detect light emitted from a label, such as lumophore molecules, for example, that have been tagged to conjugate molecules which, in turn, have been constructed to react with a specific item of interest or analyte molecules in a sample. Luminescence or generation of a light signal is achieved through addition of an activator reagent (sometimes referred to as a "trigger") and subsequent chemical reaction with any lumophore tagged molecules present in a container, such as a reaction vessel. The luminescent light or light signal produced during such a reaction may be directly or indirectly proportional to an amount of analyte present in the sample, depending on the type of assay or determination of item of interest in the sample.

Detection of the light signal may be accomplished by using a photon counting module to measure chemical luminescence. The photon counting module, in one embodiment, may comprise a detector, such as an end window photomultiplier tube and the like, operated in a photon counting mode and an optical performance check signal source, such as a blue light emitting diode and the like. The photomultiplier tube is optically connected to the reaction vessel in a read chamber by means of a light signal collector and guide, such as a fused quartz light pipe and the like. In a particular employment, once the reaction vessel enters the read chamber, a shutter closes around the reaction vessel to block ambient or environmental light. A magnet removes magnetic particles from suspension, and trigger reagent is added to initiate the luminescent reaction or generation of the light signal.

Performance of the optical system may be determined using a dilution series of label, for instance, acridinium amide, standards. Relative light units are measured over the photon counting module's dynamic range, which may be substantially within the range of about several million to less than about 20, after dark count subtraction. Both low end photon counting module sensitivity and high end linearity may be quantitated for a given population of optical systems and may be compared to similar parameters for immunoassays requiring a low level of analyte detection and a wide calibration dynamic range.

Each photon counting module may be calibrated against a standard to correct for gain and linearity variations. Multiple data points are taken using a photon reference that closely matches a spectral distribution of the label, i.e. an acridinium and the like. These data points may be used to normalize a response against the standard and to determine a required linearity correction parameter.

FIG. 1 illustrates an exemplary construction of an embodiment of an optical system 20. In this embodiment, components of the optical system 20 are located in a housing 1, which may be made of an injection molded polymer and the like. The housing 1 incorporates a labyrinth seal 2 at its outer perimeter. The seal 2 maintains substantially light tight conditions within the interior of the housing 1.

The housing 1 includes an internal chamber 3, also bounded by a labyrinth seal 4. The internal chamber 3 houses elements which direct light, shown in dotted lines in FIG. 1, from a calibration signal source or check signal source 5, which may be a blue light emitting diode and the like. The check signal source 5 may be mounted on a printed circuit board 6 to facilitate assembly of the optical system 20.

A photon counting module 7 comprises a photomultiplier tube, a photomultiplier tube socket, a voltage divider circuit, a high voltage power supply, a high gain AC amplifier, a discriminator, a reference voltage, a pulse shaper and a prescaler, not shown in FIG. 1 for clarity. Output from the prescaler is connected to a high speed digital counter which is used to count a number of photon pulses. Light, such as light from the check source 5, light signal emissions from a sample in a reaction vessel, etc., are gathered and guided to the photomultiplier tube by a light gatherer and guider or light pipe 8. The light pipe 8 is maintained in a desired orientation by an end cap 9 which contains seals 10 and 11. The seals 10 and 11 reduce the likelihood that liquids or other contaminates might enter the housing 1.

In an exemplary embodiment, the photon counting module 7 may be Part Number: P30CWAD5-07 available from THORN EMI Electron Tubes Ltd. of Middlesex, England. The light pipe 8 is available from Collomated Holes, Inc. of Campbell, Calif. The check source 5 may be Part Number: NLPB300A from Nichia Chemical Industries, LTD. of Tokushima, JAPAN.

Intensity of the check source 5 is adjusted by using a silicon photodiode 12 and analog electronics disposed on a printed circuit board 13. In a particular embodiment, the photodiode 12 may be Part Number: OPT301M available from Burr-Brown Corporation of Tucson, Ariz.

A conductor 14 is routed from the analog electronics board 13 to a check source 5 operating board 6 to supply power to the check source 5 and form a closed loop control system for the check source 5. The light output of the check source 5 is scattered using diffuser 15 to create a lambertian source. In a particular embodiment, the material comprising the diffuser 15 may be 500 grit ground glass and the like. Alternate materials, such as opal glass and the like, may also be used. In a specific embodiment, the diffuser 15 may be Part Number: 55.3000available from Rolyn Optics Company of Covina, Calif.

The scattering provided by the diffuser 15 decreases optical system 20 sensitivity to position between the check source 5 image and the silicon photodiode 12. This scattering creates a system of random illumination across the surface of the light pipe 8 at the check source 5 signal entrance location 30 and therefore makes the optical system 20 tolerant to manufacturing variations. The check source 5 signal is not focused onto the light pipe 8, rather the check source 5 signal randomly illuminates a portion outer surface area of the light pipe 8 at the entrance location 30.

Light exiting the diffuser 15 illuminates the silicon photodiode 12 after passing through a first glass plate 16. This first glass plate 16 acts as a beam splitter and is offset at an angle measuring about 45degrees with respect to a line intersecting the check source 5 and the photodiode 12. Light striking the silicon photodiode 12 produces a photocurrent proportional to an adjustable reference voltage on the analog electronics board 13.

A portion of the light striking the first glass plate 16 is reflected toward a second glass plate 17 also offset at an angle measuring about 45 degrees. The second glass plate 17 reflects a portion of the light striking the second glass plate 17 toward a third glass plate 18 offset at an angle measuring about 45 degrees. After striking the third glass plate 18, the light reflected from the surface of the third glass plate 18 is optically coupled to a side of the light pipe 8 at the entrance location 30. The area of illumination that subtends the light pipe 8 at the entrance location 30 is, in an exemplary embodiment, approximately 0.076 square inches. The entrance location 30 is positioned along a portion of a circumference of the light pipe 8 such that the check source 5 signal enters the light pipe 8 at the entrance location 30 substantially along a radius or at the side of the light pipe 8. It is to be noted that the check source 5 signal does not enter the light pipe substantially along an axis or at an end of the light pipe 8.

The light striking the side of the light pipe 8 is optically coupled, i.e. gathered and guided, into the photomultiplier tube for checking performance of the photon counting module 7. A shutter mechanism 19 may be provided to protect a photocathode of the photomultiplier tube from direct exposure to ambient light during installation, removal, cleaning, etc. of the light pipe 8.

Figure 2:
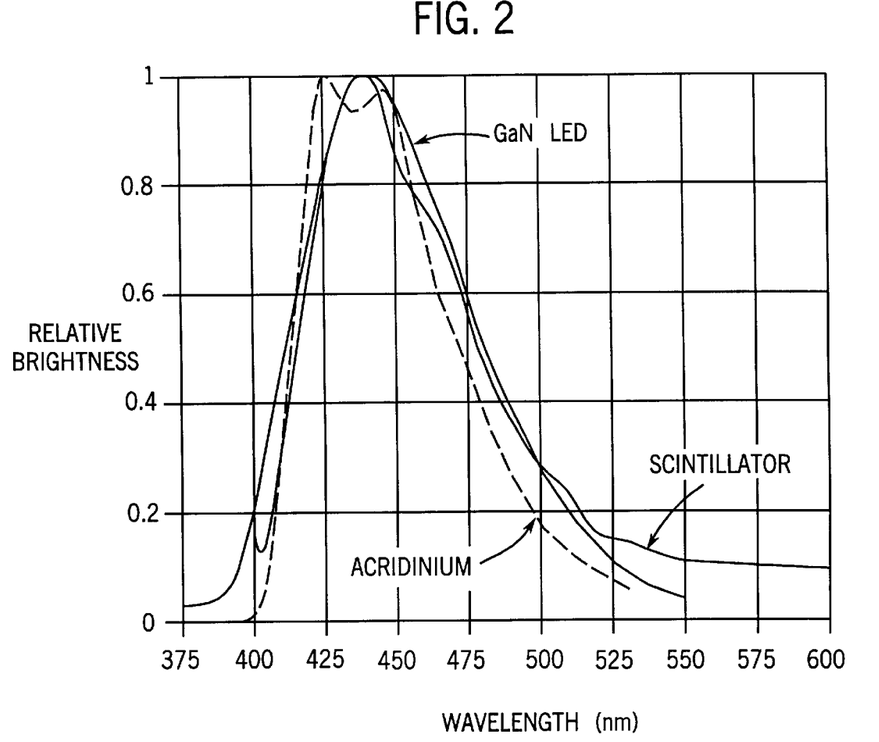
FIG. 2 is spectral distribution of acridinium.

In a specific embodiment, a gallium nitride blue light emitting diode was selected as the check source 5 because its output closely or substantially matches the spectral distribution of acridinium, which is shown in FIG. 2. By substantially matching the output of the check source 5 with the spectral distribution of a given marker to be used with the optical system 20, a probability of generating errors in optical system 20 normalization due to varying spectral responses of various photomultiplier tubes is reduced. Put more generally, the check source 5 may be chosen such that the check signal generated by the check source 5 is substantially matches, in relevant aspects, the light signal to be detected by the detector (photomultiplier tube) comprising the optical system 20.

Figure 3:
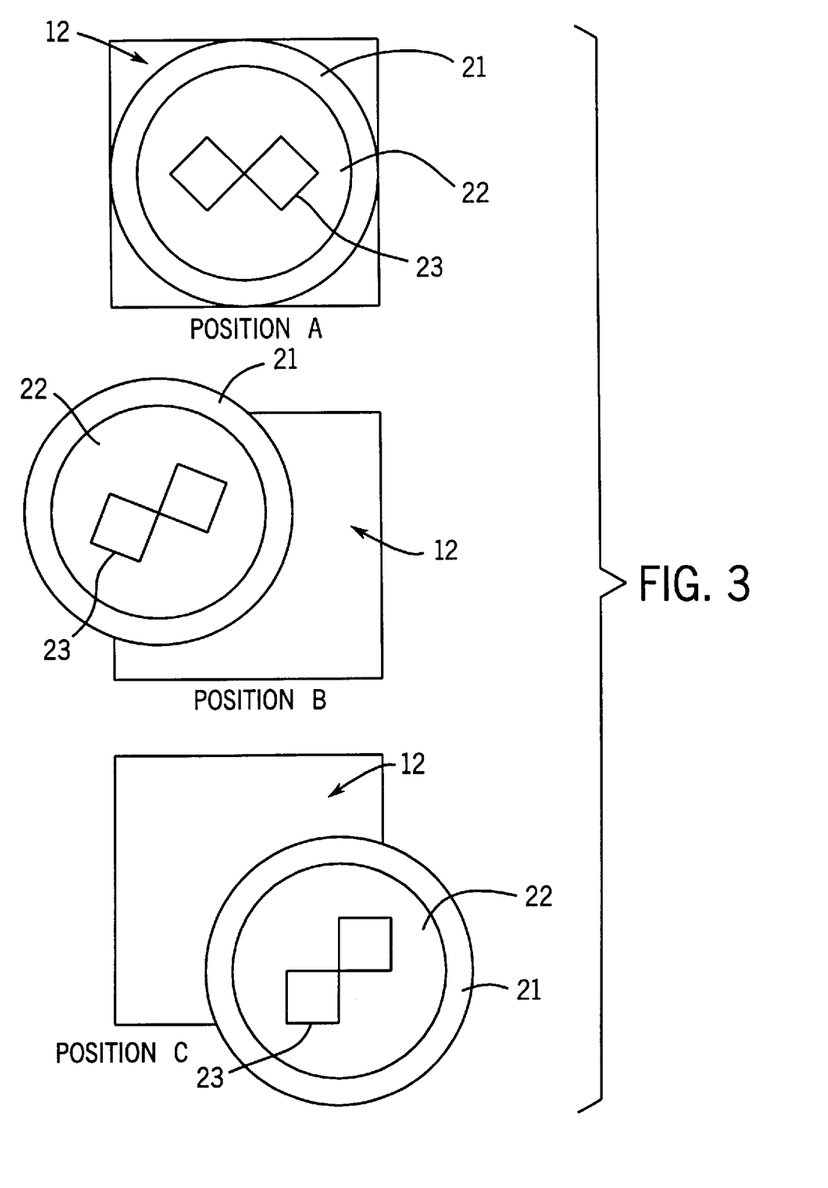
FIG. 3 is a representation of an image pattern of an element optical system of FIG. 1.

An image of the check source 5 has a pattern substantially similar to that shown in FIG. 3. The pattern comprises rings of varying intensity 21 and 22 and a center 23 of an image of the check source 5. This pattern can shift across the surface of the silicon photodiode 12 due to variations in, e.g., check source 5 construction, check source 5 positioning, photodiode 12 positioning, and glass plate 16 (beam splitter) tolerances, etc. These variations may effect photodiode 12 response. Photodiode 12 response variations, in turn, can contribute to a significant control response difference from one optical system 20 to another.

To reduce an effect of such variations, the diffuser 15 is placed in front of the check source 5. Light that strikes the diffuser 15 is scattered in all directions, thereby appearing to have substantially the same brightness when viewed at any angle. A perfect diffuser, or lambertian source, will have a brightness at any angle whose radiation per unit area is defined by $I_o \cos q$, where $I_o$ is the intensity of an element of area in a direction perpendicular to the surface and q is the angle to the surface normal. The partial diffusion properties of the diffuser 15 are sufficient to provide an effective lambertian source of light.

Light exiting the diffuser 15 strikes the first glass plate 16, offset at an angle of about 45 degrees, which acts as a beam splitter, thereby separating the incident light beam from one beam into two. A portion of the light is transmitted through the first glass plate 16 and a portion is reflected. The portion of the light which is reflected from the surface of the first glass plate 16 is given by the Fresnel reflection equation below:

$$R = \frac{1}{2} \left[ \frac{\sin^2(I-I')}{\sin^2(I+I')} + \frac{\tan^2(I-I')}{\tan^2(I+I')} \right] \quad [1]$$

where I and I' are the angles of incidence and refraction.

For the optical system 20, I=45 degrees and I'≅27.7 degrees. Using the above equation yields a reflection value of approximately 5.3%. Therefore, the amount of energy transmitted to the photodiode 12 is given by the equation T=1−R or 94.7%. Allowing a majority of the energy to be transmitted to the photodiode 12 serves three main purposes:

1] Allows enough energy to pass to the photodiode 12 so the signal-to-noise ratio of the photodiode 12 is not significant.

2] Allows the gain of a transimpedance amplifier to be a reasonable value.

3] Provides a method of attenuating the light to a level which is acceptable to the photon counting module 7.

The multiple glass plates, three in this embodiment, provide a means of steering the light beam from the check source 5 to the light pipe 8. However, the multiple glass plates 16, 17 and 18 attenuate the light emitted by the check source 5 to a level acceptable to the photon counting module 7. At the wavelengths of interest, each glass plate 16, 17 and 18 can be treated as having a substantially uniform spectral transmission (neutral density) with an optical density (O.D.) given per the following formula:

$$O.D. = \log 1/T \quad [2]$$

where T is the amount of reflected energy.

In a particular embodiment, each glass plate 16, 17 and 18 then has an O.D. value of approximately 1.276. The diffuser 15 has a total transmission of approximately 70% which equates to an O.D. value of about 0.155. An approximation of the effective total density of the optical system 20 can be given as the sum of the individual densities. Therefore, the optical system 20 O.D. is approximately 3.983 from the check source 5 to the light pipe 8. This means is that only about 0.01% of the light from the check source 5 strikes the side of the light pipe 8 at the entrance location 30.

The light striking the side of the light pipe 8 can be treated as skew rays. These skew rays rotate with each reflection with the amount of rotation being dependent on the entrance position and angle. A portion of the light will eventually emerge from the end of the light pipe 8 closest to the photomultiplier tube.

Figure 4:
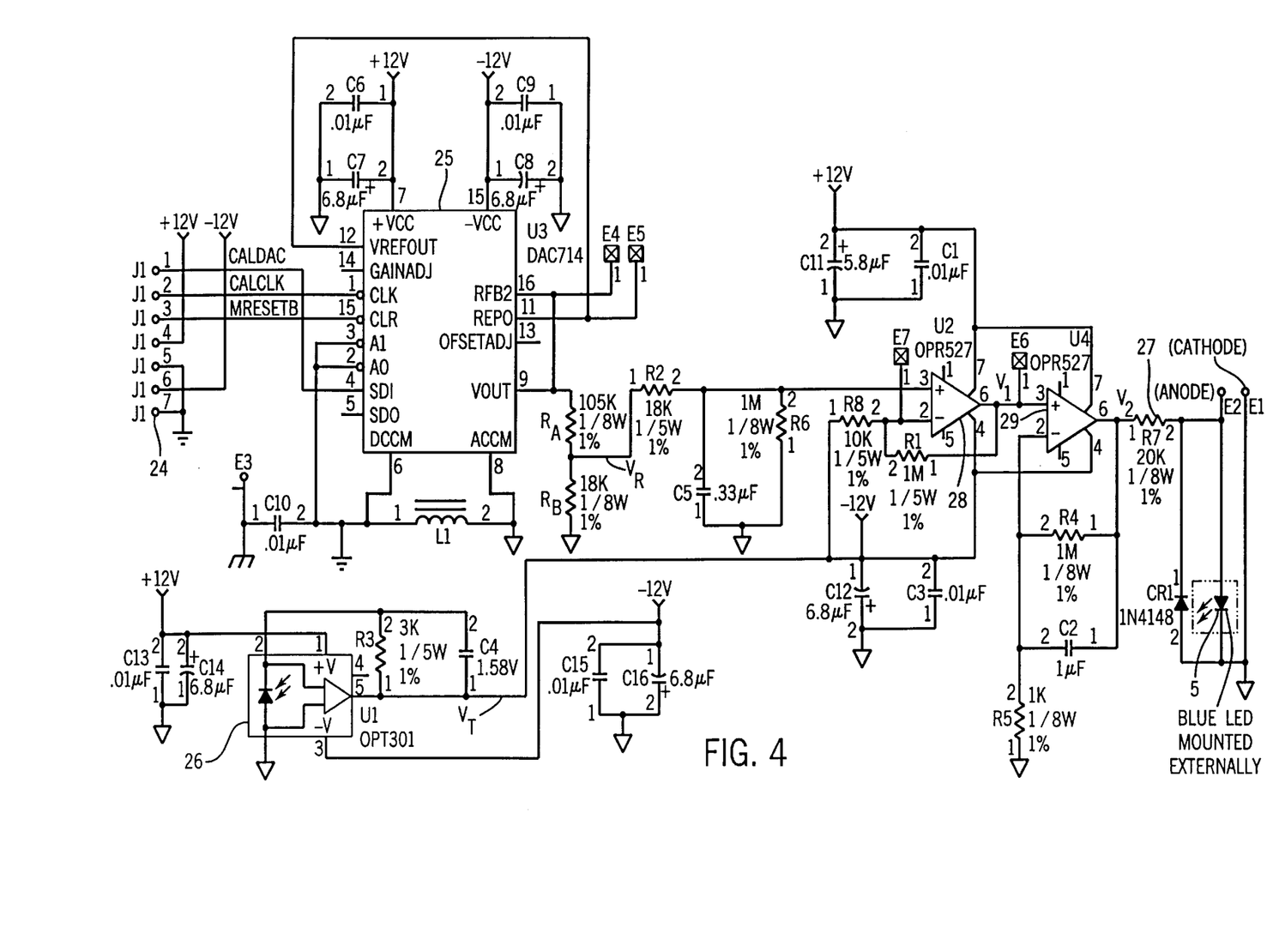
FIG. 4 is as schematic diagram of a portion of the optical system of FIG. 1.

The electronics used to control the check source 5 are shown in FIG. 4. Input power and control signals to the analog electronics board 13 come in through connector Ji, indicated by reference character 24, on the printed circuit board 13. The circuit requires +12 Vdc, −12 Vdc and ground for power with a 16-bit Digital-to-Analog Converter (DAC) 25 with serial data interface requiring the following additional lines: Clear, Serial Data Clock and Serial Data Input signals. The output of the DAC 25 is used as a reference voltage to control the intensity of the check source 5 and is operated in the bipolar mode with an output range of −5 Vdc to +5 Vdc. The bipolar mode was chosen to provide a method of turning the check source 5 off completely because of the offset voltages and currents of the various components in the circuit. This method reduces a need to manually adjust the circuit using, for instance, potentiometers.

In an exemplary embodiment, the silicon photodiode 12 is an opto-electronic device containing a photodiode and transimpedance amplifier on a single chip 26. The photodiode 12 current is wavelength dependent, is defined as the responsivity in amperes/watt (A/W), and is proportional to the radiant power (watts) falling on the photodiode 12. Therefore, the final photodiode 12 current becomes a convolution between the spectral output of the check source 5 and the responsivity of the photodiode 12. Selected as a balance between signal-to-noise ratio, signal bandwidth and elimination of any special board design or handling requirements, the transimpedance amplifier has a gain of about $30 \times 10^6$. The dynamic range of the reference voltage can be adjusted by connecting a power supply to the check source 5 current limiting resistor 27 and varying the voltage so a count value at the upper range of linearity for the photon counting module 7 is achieved.

The resolution of the reference voltage, or Least Significant Bit (LSB), due to the DAC 25, can be calculated as follows:

$$LSB = \frac{\text{OutputVoltageRange}}{2^{\text{NumberofBits}}} = \frac{10 \text{ V}}{2^{16}} \approx 153 \, \mu V \quad [3]$$

The final resolution of the reference voltage used to control the check source 5 intensity is adjusted using resistors RA and RB (FIG. 4):

$$LSB_{Final} = LSB * \left[ \frac{R_B}{R_A + R_B} \right] = 13.9 \, \mu V \quad [4]$$

This reduces the dynamic range of the reference voltage to substantially within the range of −454 mV to +454 mV. The output of the transimpedance amplifier and the reference voltage are applied to differential DC amplifier 28. Assuming ideal conditions and noting that R1/R8=R6/R2, the output voltage reduces to $$V_1 = \left[ \frac{R1}{R8} \right] * (V_T - V_R) \quad [5]$$

The output of the differential DC amplifier 28 is applied to noninverting amplifier 29. Again, assuming ideal conditions, the output voltage becomes:

$$V_2 = \left[ 1 + \frac{R4}{R5} \right] * (V_1) \quad [6]$$

Combining these two equations yields the voltage that drives the check source 5:

$$V_2 = \left[ 1 + \frac{R4}{R5} \right] * \left[ \frac{R1}{R8} \right] * (V_T - V_R) \quad [7]$$

The voltage of the transimpedance amplifier is:

$$V_T = R3 * I_{photodiode} \quad [8]$$

where, because of output scaling, $$I_{photodiode} = \frac{V_2}{R3} \quad [9]$$

therefore, the transimpedance output is equal to the voltage driving the check source 5, $$V_T = V_2 \quad [10]$$

Inserting this relationship into equation [7] above and solving for V2 shows the relationship between the reference voltage and check source 5 drive voltage:

$$V_2 = \frac{V_R}{\left( 1 - \frac{1}{\left[ 1 + \frac{R4}{R5} \right] * \left[ \frac{R1}{R8} \right]} \right)} \quad [11]$$

At low frequencies, where loop gain is high, the closed loop gain is determined by the feedback network. Equation [11] shows that the drive voltage to the check source 5 is equal to the reference voltage when the gain of the feedback network is large. Solving equation [11] yields:

$$V_2 = 1.00001 V_R \quad [12]$$

At low frequencies, the fractional part in the denominator approximates the gain error. For this system, the fractional part is substantially equal to about 100,100 or 100dB, which equates to a gain error of approximately 0.001%.

Table 1 shows the spice pole/zero analysis of the closed loop system.

TABLE 1

Spice Plus Version 3.1.6
CIRCUIT NAME: OPA627 -- START OF DECK
PZ analysis.

GAIN = 0.90089

| POLES (HZ) | Input = S | Output = D, 0 | xxxxxxxxxxxxxxxxxxxxxx | |
|---|---|---|---|---|
| # | REAL | IMAG | MAG (HZ) | PHASE (DEG) |
| 1 | −2.57450e + 01 | 0.00000e + 00 | 2.57450e + 01 | 180 |
| 2 | −1.53552e + 02 | 1.44671e + 02 | 2.10969e + 02 | 136.71 |
| 3 | −1.53552e + 02 | −1.44671e + 02 | 2.10969e + 02 | −136.71 |
| 4 | −2.07695e + 03 | 0.00000e + 00 | 2.07695e + 03 | 180 |
| 5 | −2.07696e + 03 | 4.39471e − 03 | 2.07696e + 03 | 180 |
| 6 | −2.07696e + 03 | −4.39471e − 03 | 2.07696e + 03 | −180 |
| 7 | −1.66619e + 05 | 0.00000e + 00 | 1.66619e + 05 | 180 |
| 8 | −8.46518e + 05 | 0.00000e + 00 | 8.46518e + 05 | 180 |
| 9 | −4.33646e + 06 | 0.00000e + 00 | 4.33646e + 06 | 180 |
| 10 | −1.52124e + 07 | 0.00000e + 00 | 1.52124e + 07 | 180 |
| 11 | −1.88109e + 07 | 0.00000e + 00 | 1.88109e + 07 | 180 |
| 12 | −1.88110e + 07 | 0.00000e + 00 | 1.88110e + 07 | 180 |
| 13 | −2.97395e + 07 | 8.23882e + 06 | 3.08596e + 07 | 164.52 |
| 14 | −2.97395e + 07 | −8.23882e + 06 | 3.08596e + 07 | −164.52 |
| 15 | −5.94630e + 07 | 0.00000e + 00 | 5.94630e + 07 | 180 |
| 16 | −2.28514e + 08 | 0.00000e + 00 | 2.28514e + 08 | 180 |
| 17 | −9.94344e + 08 | 0.00000e + 00 | 9.94344e + 08 | 180 |

| ZEROS (HZ) | Input = S | Output = D, 0 | ooooooooooooooooooooooo | |
|---|---|---|---|---|
| # | REAL | IMAG | MAG (HZ) | PHASE (DEG) |
| 1 | −2.79222e + 01 | 0.00000e + 00 | 2.79222e + 01 | 180 |
| 2 | −1.59314e + 02 | 0.00000e + 00 | 1.59314e + 02 | 180 |
| 3 | −2.07695e + 03 | 0.00000e + 00 | 2.07695e + 03 | 180 |
| 4 | −2.07696e + 03 | 3.87238e − 03 | 2.07696e + 03 | 0.00010683 |
| 5 | −2.07696e + 03 | −3.87238e − 03 | 2.07696e + 03 | −0.00010683 |
| 6 | −8.43968e + 05 | 0.00000e + 00 | 8.43968e + 05 | 180 |
| 7 | −4.33721e + 06 | 0.00000e + 00 | 4.33721e + 06 | 180 |
| 8 | −1.52145e + 07 | 0.00000e + 00 | 1.52145e + 07 | 180 |
| 9 | −1.88109e + 07 | 0.00000e + 00 | 1.88109e + 07 | 180 |
| 10 | −1.88109e + 07 | 0.00000e + 00 | 1.88109e + 07 | 180 |
| 11 | −2.28514e + 08 | 0.00000e + 00 | 2.28514e + 08 | 180 |

The analysis shows that all zeros are in the Left-Hand-Plane (LHP) for a minimum phase transfer function and there are no poles in the Right-Hand-Plane (RHP).

Figure 5:
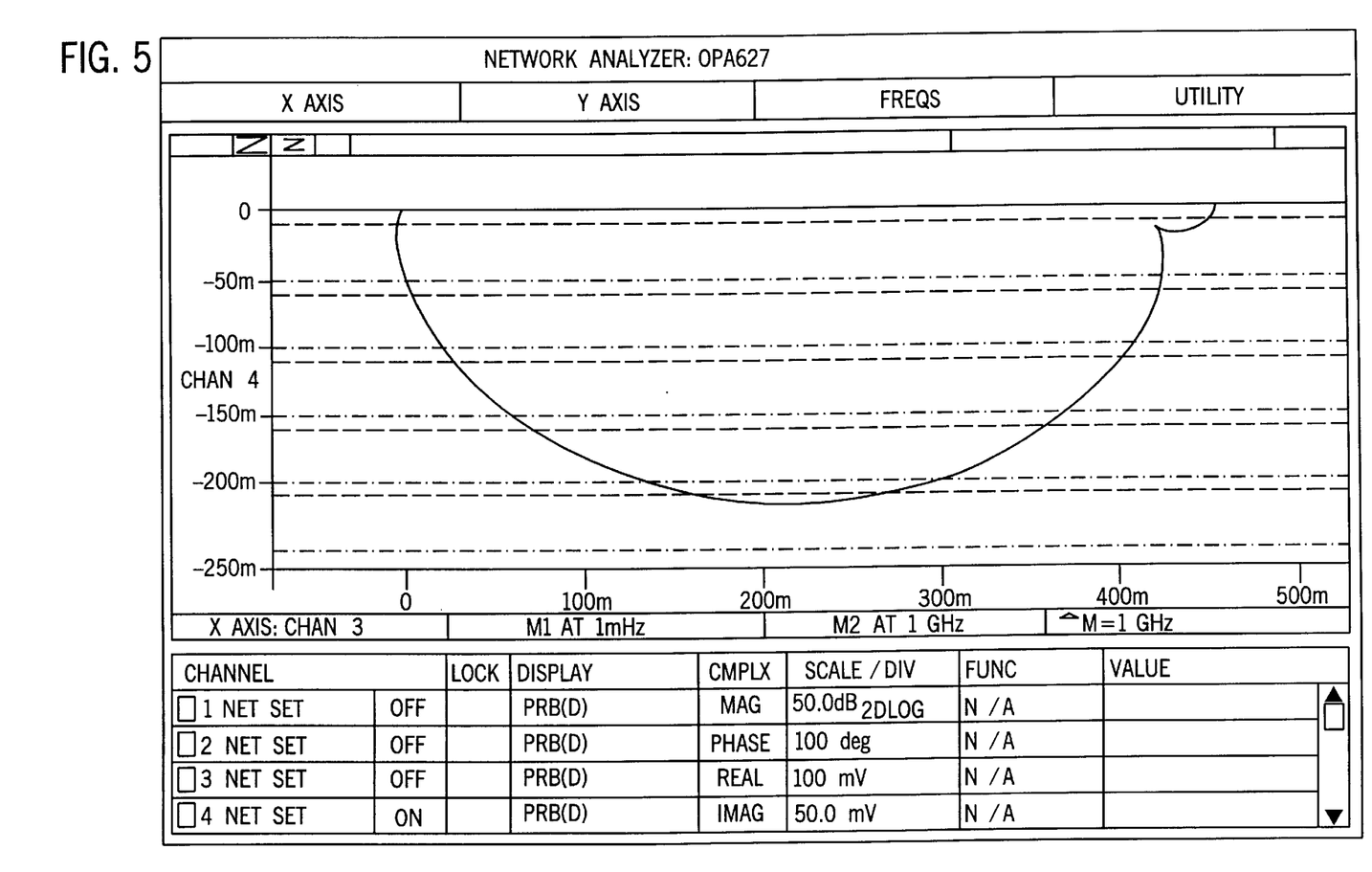
FIG. 5 is a polar plot of a frequency response around a feedback loop comprising the optical system of FIG. 1.

FIG. 5 is a polar plot of the frequency response around the feedback loop. The Nyquist stability criterion was used on this plot to determine the stability of the linear control system. When a system has no poles in the RHP, then the feedback system is stable if and only if the contour does not encircle the −1,0 point. Per this criterion, the plot represents a stable system with infinite gain margin.

Figure 6:
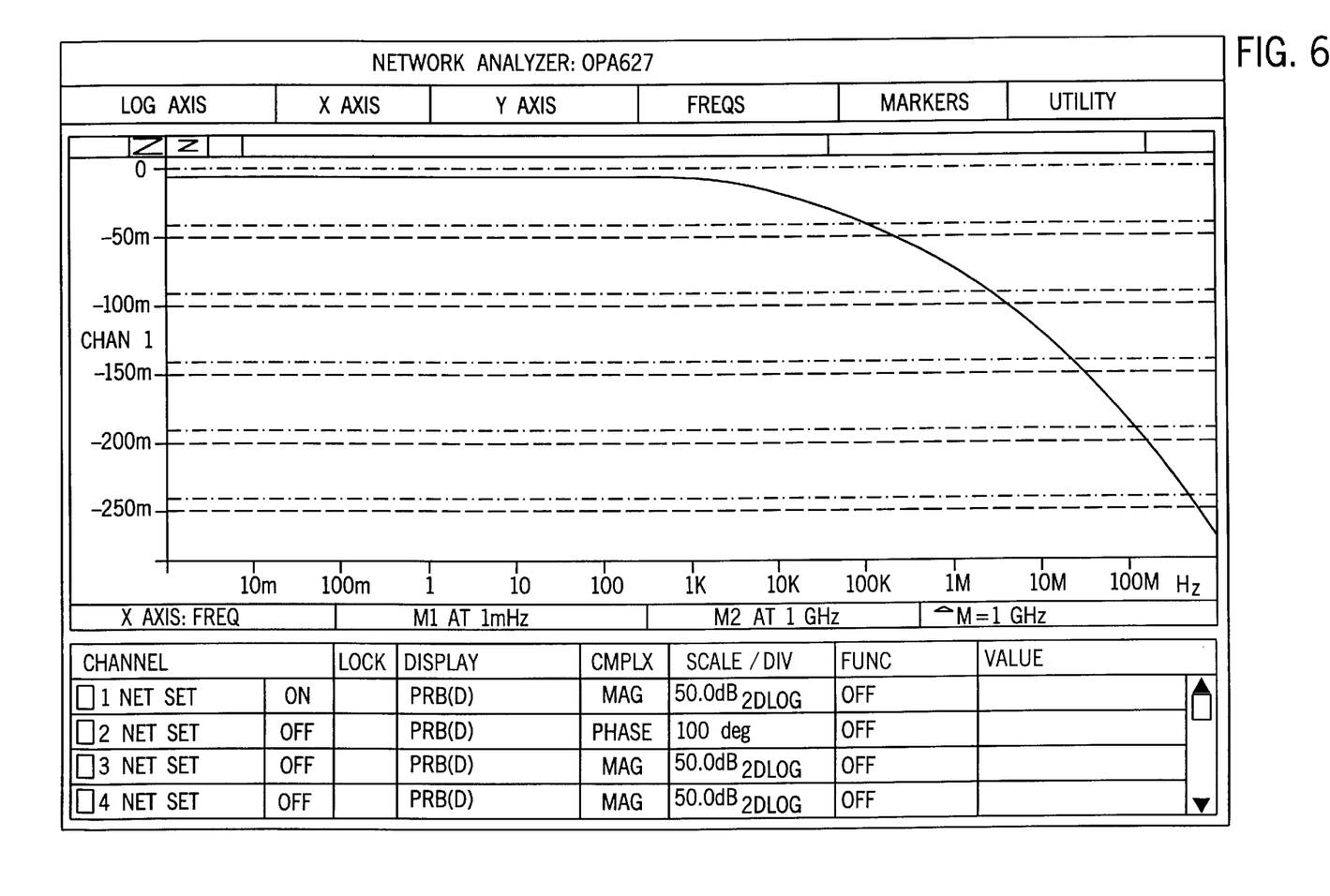
FIGS. 6 and 7 show magnitude and phase response, respectively, of a transfer function using Bode plots.
Figure 7:
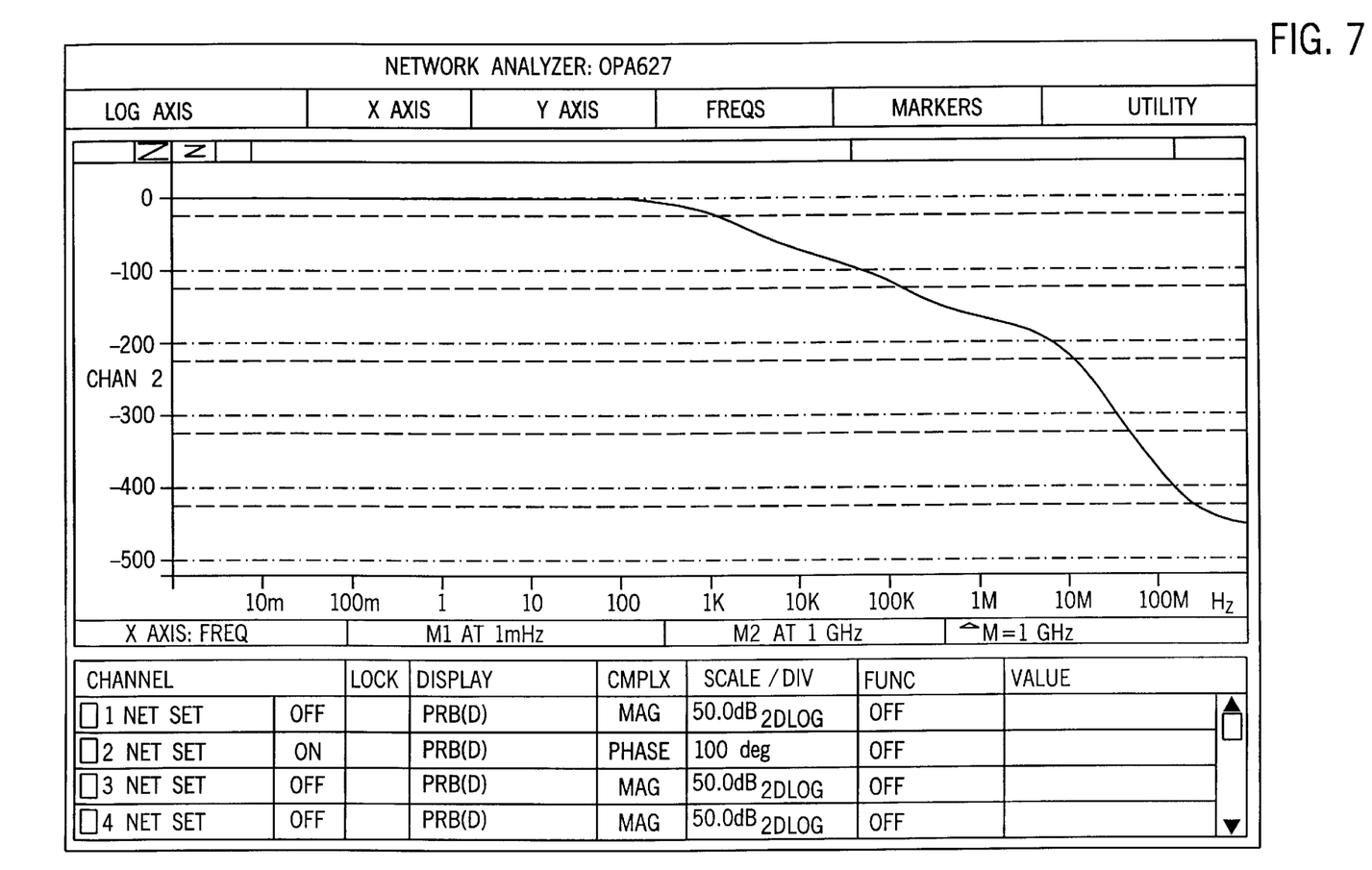

FIGS. 6 and 7 show the magnitude and phase response, respectively, of the transfer function using Bode plots. The magnitude plot shows that the break frequency, or b 3dB frequency, is approximately 2.5 Khz.

Figure 8:
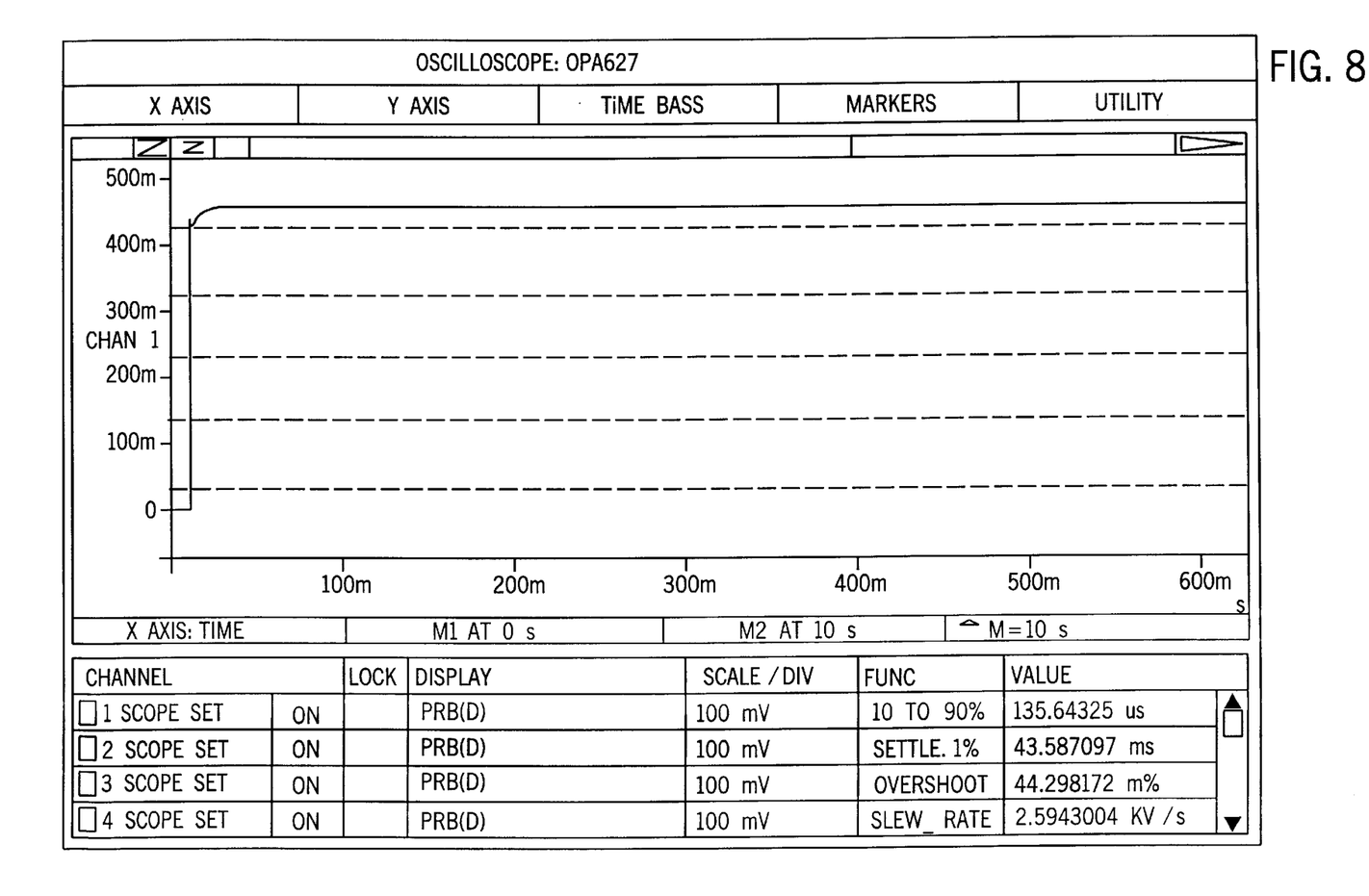
FIG. 8 represents transient response of the optical system of FIG. 1 with respect to a step input.

Even though an optical system 20 may be stable, it is also desirable to determine if the transient response is acceptable. FIG. 8 represents the transient response of the optical system 20 with respect to a step input. The transient response shows that the optical system 20 settles within about 0.1% within about 44 ms with minimal overshoot.

In one instance, during calibration of the photon counting module 7, the check source 5 is adjusted to various intensity levels within the linear range of the photomultiplier tube using the DAC 25. Prior to turning the check source 5 on, a background reading is taken. The output pulses of the photomultiplier tube are integrated over approximately 3 seconds using about 0.1 second intervals at each intensity level. A linear regression is performed on the data to determine a slope in Relative Light Units/DAC after it has been normalized to a standard and background corrected. This slope value is then stored in the optical system 20.

During initialization of an instrument using the optical system 20 or other diagnostic procedures, for example, the DAC 25 is incremented using the same values defined during calibration. A linear regression is again performed on the data to determine a slope after it has been normalized and background corrected. Maintenance or repair is desirable when the slope changes by a predetermined percentage from the predetermined slope.

While a specific embodiment of the optical system 20 has been described to facilitate understanding, it is to be noted that the optical system 20 can be modified to meet particulars of a given employment.

What is claimed is:

1. An optical system comprising:
   (a) a detector for detecting a light signal;
   (b) a light signal gatherer and guider optically connected with the detector (a) for gathering the light signal and guiding the light signal to the detector (a), the light signal gatherer and guider (b) having an outer surface and an end;

(c) a check signal entrance location disposed along the outer surface of the light signal gatherer and guider (b); and (d) a check signal source optically connected with the light signal gatherer and guider (b) so that a check signal generated by the check signal source (c) randomly illuminates check signal entrance location on the outer surface of the light signal gatherer and guider (b).

2. An optical system as defined in claim 1 wherein the detector (a) is a photomultiplier tube.

3. An optical system as defined in claim 1 wherein the light signal gatherer and guider (b) is a light pipe.

4. An optical system as defined in claim 1 wherein the check signal generated by the check signal source (c) substantially matches the light signal detected by the detector (a).

5. An optical system as defined in claim 1 wherein the check signal is blue.

6. An optical system as defined in claim 1 wherein the check signal source (c) is a light emitting diode.

7. An optical system as defined in claim 1 wherein the check signal source (c) is a gallium nitride blue light emitting diode.

8. An optical system as defined in claim 1 wherein the check signal entrance location measures approximately 0.076 square inches.

9. An optical system as defined in claim 1 further comprising:

(e) a diffuser optically located between the check signal source (d) and the light signal gatherer and guider (b).

10. An optical system as defined in claim 1 further comprising:

(e) a photodiode optically connected with the check signal source (d) for receiving the check signal; and (f) a beam splitter optically located between the check signal source (d) and the photodiode (e) for splitting the check signal such that a first portion of the check signal is optically applied to the check signal entrance location and a second portion of the check signal is optically applied to the photodiode (e).

11. An optical system as defined in claim 1 wherein the light signal gatherer and guider (b) has a radius and an axis of elongation, and wherein the check signal entrance location is disposed on the light signal gatherer and guider (b) such that the check signal enters the light signal gatherer and guider (b) substantially along the radius.

* * * * *

UNITED STATES PATENT AND TRADEMARK OFFICE
CERTIFICATE OF CORRECTION

PATENT NO. : 5,859,429
DATED : January 12, 1999
INVENTOR(S) : Brown et al.

It is certified that error appears in the above-identified patent and that said Letters Patent is hereby corrected as shown below:

Column 9, line 7, change "illuminates check"
to --illuminates the check--.

Signed and Sealed this

Twentieth Day of July, 1999

Attest:

Attesting Officer

Q. TODD DICKINSON

Acting Commissioner of Patents and Trademarks